(12) United States Patent
Mason et al.

(10) Patent No.: US 6,787,303 B1
(45) Date of Patent: Sep. 7, 2004

(54) IDENTIFICATION OF A NOVEL RETROVIRUS ASSOCIATED WITH PRIMARY SCLEROSING CHOLANGITIS AND AUTOIMMUNE HEPATITIS

(75) Inventors: Andrew L. Mason, New Orleans, LA (US); Lizhe Xu, Metairie, LA (US); Linsheng Guo, Metairie, LA (US)

(73) Assignee: Alton Ochsner Medical Foundation, New Orleans, LA (US)

( * ) Notice: Subject to any disclaimer, the term of this patent is extended or adjusted under 35 U.S.C. 154(b) by 0 days.

(21) Appl. No.: 09/536,552

(22) Filed: Mar. 28, 2000

Related U.S. Application Data

(60) Provisional application No. 60/127,347, filed on Apr. 1, 1999.

(51) Int. Cl.[7] .............................. C12Q 1/70; C12Q 1/68; C07H 21/04
(52) U.S. Cl. .............................. 435/5; 435/6; 536/23.1; 536/24.3
(58) Field of Search ...................... 435/5, 7.1, 6, 91.31, 435/325, 375; 514/44; 536/24.5, 23.1, 24.33, 24.3

(56) References Cited

U.S. PATENT DOCUMENTS

| | | |
|---|---|---|
| 5,800,980 A | 9/1998 | Perron et al. |
| 5,830,667 A | 11/1998 | Alvarez |
| 5,919,701 A * | 7/1999 | Peterson |
| 6,083,685 A | 7/2000 | Petrik |

OTHER PUBLICATIONS

Mason et al. The Lancet, vol. 351, pp. 1620–1624, Mar. 1998.*

Stanley Crooke, Antisense Research and Applications, Chapter 1, Basic Principles of Antisense Therapeutics, Springer–Verlag Press, Berlin, Heidelberg, New York, p. 3, Jul. 1998.*

Brookes et al., 1992, "The immune response to and expression of cross–reactive retroviral GAG sequences in autoimmune disease", Brit J Rheum 31:735–742.

Czaja, 1998, "Frequency and nature of the variant syndromes of autoimmune liver disease", Hepatology 28(2):360–365.

Gueguen et al., 1988, "Anti–liver kidney microsome antibody recognizes a cytochrome P450 from the IID subfamily", J Exp Med 168(2):801–6.

Gueguen et al., 1989, "Anti–liver–kidney microsome antibody type 1 recognizes human cytochrome P450 db1", Biochem Biophys Res Commun 159(2):542–7.

Harmatz et al., "Hepatobiliary manifestations of inflammatory bowel disease", Med Clin North Am. 78(6):1387–98 (1989).

Manns, 1997, "Recent developments in autoimmune liver diseases", J Gastroenterol Hepatol 12:S256–271.

Putnam, 1996, "Antisense strategies and therapeutic applications", Am J Health–Syst Pharm 53:151–183.

Rasmussen et al., 1997, "Possible involvement of endogenous retroviruses in the development of autoimmune disorders, especially multiple sclerosis", Acta Neurol Scand 169:32–37.

Waxman et al., 1988, "Antibodies to liver/kidney microsome1 in chronic active hepatitis recognize specific forms of hepatic cytochrome P–450", Gastroenterology 95(5):1326–31.

Zanger et al., 1988, "Antibodies against human cytochrome P–450db1 in autoimmune hepatitis type II", Proc Natl Acad Sci U S A 85(21):8256–60.

* cited by examiner

*Primary Examiner*—Sean McGarry
*Assistant Examiner*—Janet L. Epps-Ford
(74) *Attorney, Agent, or Firm*—Jones Day

(57) ABSTRACT

The present invention relates first, to the identification of a retrovirus and the novel nucleotide sequences encoding a retroviral polymerase gene (POL nucleotides) associated with the existence of primary sclerosing cholangitis (PSC), autoimmune hepatitis (AIH) Crohn's disease and ulcerative colitis. The present invention further relates to methods for using the PSC associated retroviral nucleotides for the detection of PSC, AIH, Crohn's disease and ulcerative colitis in patient samples. The present invention also relates to methods for using and targeting the PSC associated retroviral POL nucleotides in gene therapy protocols for the treatment of PSC, AIH, Crohn's disease or ulcerative disease in patients in need of such treatment. The present invention further relates to diagnostic protocols and kits for the detection of PSC, AIH, Crohn's disease and ulcerative colitis in tissue samples.

4 Claims, 1 Drawing Sheet

Figure 1:
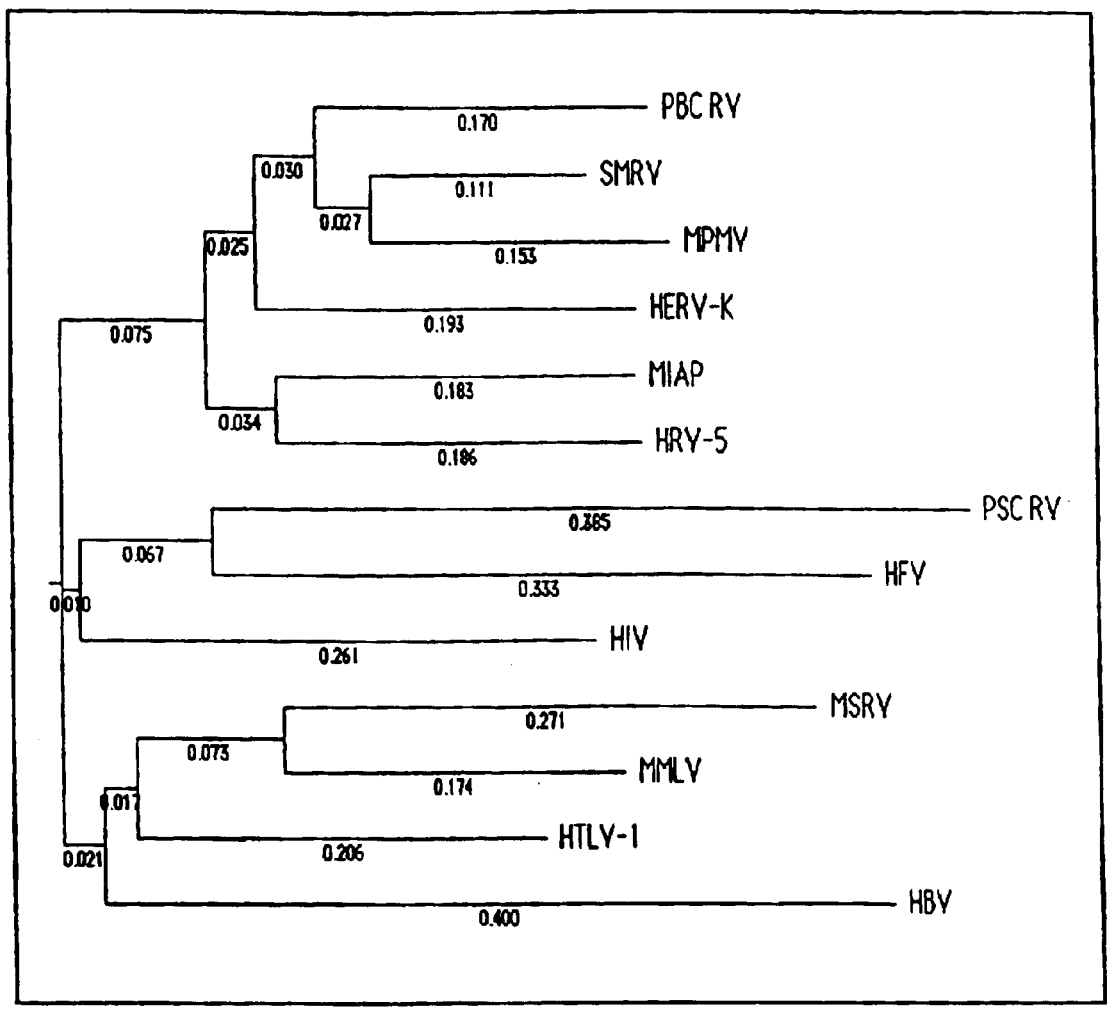

SEQUENCE LISTING

<160> NUMBER OF SEQ ID NOS: 12

<210> SEQ ID NO 1
<211> LENGTH: 126
<212> TYPE: DNA
<213> ORGANISM: Artificial Sequence
<220> FEATURE:
<223> OTHER INFORMATION: OB1-DP52r clone

<400> SEQUENCE: 1
tggaaggtgt taccacaggg ataaagtttc taatcaattc acctatggtt atattcattt     60
attcgactcc tttctcttta ttcctcacca ttaattttct tgcccaagta catggatgac    120
ctccct                                                                126

<210> SEQ ID NO 2
<211> LENGTH: 125
<212> TYPE: DNA
<213> ORGANISM: Artificial Sequence
<220> FEATURE:
<223> OTHER INFORMATION: OB1-DP54 clone

<400> SEQUENCE: 2
tggaaggtgc tgccacaagg ataaagtttc caatcaattc acctatggtt atattcattt     60
attcgactcc tttctcttta ttcctcacca ttaattttct tgcccaagta catggatgac    120
ctccc                                                                 125

<210> SEQ ID NO 3
<211> LENGTH: 124
<212> TYPE: DNA
<213> ORGANISM: Artificial Sequence
<220> FEATURE:
<223> OTHER INFORMATION: OB1-DP55 clone

<400> SEQUENCE: 3
tggaaggtgt tgccacaagg ataaagtttc caatcaattc acctatggtt atattcattt     60
attcgactcc tttctcttta ttcctcacca ttaattttct tgcccaagta catggatgac    120
atca                                                                  124

<210> SEQ ID NO 4
<211> LENGTH: 121
<212> TYPE: DNA
<213> ORGANISM: Artificial Sequence
<220> FEATURE:
<223> OTHER INFORMATION: NB6-e27.3r clone
<221> NAME/KEY: modified_base
<222> LOCATION: (1)...(121)
<223> OTHER INFORMATION: n=a, c, g, or t

<400> SEQUENCE: 4
tttggaaggt gttgccanag ggatgaagtt tccaatcgaa ttcacctatg gttatattca     60
tttattcgac tcctttctct ttattcctca ccattaattt tcttgcccaa gtacatggat    120
g                                                                     121

<210> SEQ ID NO 5
<211> LENGTH: 101
<212> TYPE: DNA
<213> ORGANISM: Artificial Sequence
<220> FEATURE:
<223> OTHER INFORMATION: NB6-e27.4r clone

```
<400> SEQUENCE: 5
aggataaagt tccaatcga attcacctat ggttatattc atttattcga ctcctttctc      60
tttattcctc accattaatt ttcttgccca agtacatgga t                         101

<210> SEQ ID NO 6
<211> LENGTH: 120
<212> TYPE: DNA
<213> ORGANISM: Artificial Sequence
<220> FEATURE:
<223> OTHER INFORMATION: NB6-e27.5r clone

<400> SEQUENCE: 6
ctttggaagg tgttgcccca aggataaagt ttccaatcaa tgcacctatg gttatattca     60
tttattcgac tcctttctct ttattcctca ccattaattt tcttgcccaa gtacatggat    120

<210> SEQ ID NO 7
<211> LENGTH: 120
<212> TYPE: DNA
<213> ORGANISM: Artificial Sequence
<220> FEATURE:
<223> OTHER INFORMATION: NB6-e27.15r clone
<221> NAME/KEY: modified_base
<222> LOCATION: (1)...(120)
<223> OTHER INFORMATION: n=a, c, g, or t

<400> SEQUENCE: 7
tttggaaggt gttgcnnnag ggaataaagt ttccaatcga attcacctat ggttatattc     60
atttattcga ctcctttctc tttattcctc accattaatt ttcttgccca agtacatgga    120

<210> SEQ ID NO 8
<211> LENGTH: 20
<212> TYPE: DNA
<213> ORGANISM: Artificial Sequence
<220> FEATURE:
<223> OTHER INFORMATION: primer
<221> NAME/KEY: modified_base
<222> LOCATION: (1)...(20)
<223> OTHER INFORMATION: I

<400> SEQUENCE: 8
tggaangtny trccmcargg                                                 20

<210> SEQ ID NO 9
<211> LENGTH: 17
<212> TYPE: DNA
<213> ORGANISM: Artificial Sequence
<220> FEATURE:
<223> OTHER INFORMATION: primer
<221> NAME/KEY: modified_base
<222> LOCATION: (1)...(17)
<223> OTHER INFORMATION: I

<400> SEQUENCE: 9
nnnnadrtca tccatrt                                                    17

<210> SEQ ID NO 10
<211> LENGTH: 24
<212> TYPE: DNA
<213> ORGANISM: Artificial Sequence
<220> FEATURE:
<223> OTHER INFORMATION: primer

<400> SEQUENCE: 10
gtgctgccac aaggataaag tttc                                            24
```

```
<210> SEQ ID NO 11
<211> LENGTH: 22
<212> TYPE: DNA
<213> ORGANISM: Artificial Sequence
<220> FEATURE:
<223> OTHER INFORMATION: primer

<400> SEQUENCE: 11
gggaggtcat ccatgtactt gg                                    22

<210> SEQ ID NO 12
<211> LENGTH: 25
<212> TYPE: DNA
<213> ORGANISM: Artificial Sequence
<220> FEATURE:
<223> OTHER INFORMATION: primer

<400> SEQUENCE: 12
cgactccttt ctctttattc ctcac                                 25
```

IDENTIFICATION OF A NOVEL RETROVIRUS ASSOCIATED WITH PRIMARY SCLEROSING CHOLANGITIS AND AUTOIMMUNE HEPATITIS

This application claims the benefit of the earlier filing date of provisional application 60/127,347, filed on Apr. 1, 1999, pursuant to 35 U.S.C § 119(e) and hereby incorporates said provisional application by reference.

1. INTRODUCTION

The present invention relates first, to the identification of a retrovirus and the novel nucleotide sequences encoding a retroviral polymerase gene (POL nucleotides) associated with the existence of primary sclerosing cholangitis (PSC), autoimmune hepatitis (AIH) Crohn's disease and ulcerative colitis. The present invention further relates to methods for using the PSC associated retroviral nucleotides for the detection of PSC, AIH, Crohn's disease and ulcerative colitis in patient samples. The present invention also relates to methods for using and targeting the PSC associated retroviral POL nucleotides in gene therapy protocols for the treatment of PSC, AIH, Crohn's disease or ulcerative disease in patients in need of such treatment. The present invention further relates to diagnostic protocols and kits for the detection of PSC, AIH, Crohn's disease and ulcerative colitis in tissue samples.

2. BACKGROUND OF THE INVENTION

Extraintestinal complications of inflammatory bowel disease, including diseases of the liver and biliary tract, affect a large number of patients with ulcerative colitis Crohn's disease. Indeed, hepatobiliary complications may affect as many as 10 percent of patients with inflammatory bowel disease. The occurrences of specific hepatobiliary diseases associated with inflammatory bowel disease, however, vary widely; some disorders occur commonly and others rarely. The clinical significances of individual hepatobiliary disorders also vary, ranging from inconsequential to life-threatening. Current data indicate that primary sclerosing cholangitis (PSC) is the most common disease associated with either ulcerative colitis or Crohn's disease. (Harmatz A., Hepatobiliary Manifestations of Inflammatory Bowel Disease. Med. Clin. North AM 78:1387, 1994).

Primary sclerosing cholangitis (PSC) was originally defined as a chronic cholestatic liver disease characterized by fibrosing inflammation of segments of the extrahepatic bile ducts. PSC results in a progressive narrowing or obliteration of bile duct lumens, progression to secondary biliary cirrhosis, with complications of portal hypertension, hepatic failure and cholangiocarcinoma is an idiopathic disorder characterized by inflammation and obliteration of both intrahepatic and extrahepatic bile ducts. Cholangiocytes account for 3%–5% of the hepatic cell population and line a complex network of interconnecting conduits in the liver, termed the intrahepatic biliary ductal system. One of the pathological conditions manifested in both the intrahepatic and extrahepatic bile ducts is PSC.

The natural history of PSC is incompletely understood and the variability in the location of sclerotic lesions results in a wide spectrum of clinical disease. This is especially true for asymptomatic patients and the subgroup of patients with disease confined to the intrahepatic ducts. Although as many as 30 percent of patients with the disease have demonstrable autoantibodies, there is no serologic marker associated with PSC and the diagnosis is made by radiographic demonstration of irregular strictures and dialations within the bile ducts (Vierling, Hepatobiliary complications of ulcerative colitis and Crohn's disease. Third Edition. Philadelphia: W. B. Saunders, 1996). Patients invariably develop cirrhosis, the sequelae of liver failure, and 5 to 15 percent succumb to cholangiocarcinoma. At present, there is no curative medical therapy for PSC and liver transplantation is required to avoid these sequelae of endstage liver disease (Vierling, Hepatobiliary complications of ulcerative colitis and Crohn's disease. Third Edition. Philadelphia: W. B. Saunders, 1996).

In North America approximately 1 in 20,000 suffer from PSC and the majority of these patients have macroscopic or microscopic evidence of either ulcerative colitis or Crohn's disease (Vierling, Hepatobiliary complications of ulcerative colitis and Crohn's disease. Third Edition. Philadelphia: W. B. Saunders, 1996). Other hepatic disorders may occur in patients with inflammatory bowel disease in the absence of cholangiographic evidence of large bile duct disease, including autoimmune hepatitis (AIH) and pericholangitis, a non-specific histologic diagnosis of small duct PSC. (Vierling. Hepatobiliary complications of ulcerative colitis and Crohn's disease. Third Edition. Philadelphia: W. B. Saunders, 1996). AIH, pericholangitis, and PSC form the spectrum of the same hepatobiliary disorder associated with inflammatory bowel disease that may share a common etiological agent.

Autoimmune Hepatitis

An additional disease to which the present invention is directed is autoimmune hepatitis (AIH). Because there is no single diagnostic test for autoimmune hepatitis, it may initially be indistinguishable from other liver disorders. Early recognition is important, however, since patients suffering from autoimmune hepatitis benefit from treatment with immunosuppressives but not from treatment with interferons, used in the treatment of viral-induced hepatitis. Thus, the differentiation between viral-induced hepatitis and autoimmune hepatitis is important to ensure correct treatment. Autoimmune hepatitis, in particular in children, is an inflammatory disease which progresses into cirrhosis and hepatic insufficiency, which generally responds to an immunosuppressive treatment and is characterized by the presence of high non-organ-specific autoantibody titres.

Two subgroups have been defined, as a function of the autoantibody present in the serum: anti-smooth muscle antibody (anti-SMA) and anti-liver-kidney-microsome antibodies (anti-LKM), called hereinafter anti-SMA and anti-LKM antibodies.

The antigen recognized by the anti-LKM antibodies is a protein with a molecular weight of 50 kDa, which is present at a relatively high concentration in the endoplasmic reticulum. Several studies suggest that this antigen corresponds to a protein of the cytochrome P450 family (Waxman, 1988, Gastroenterol., 95: 1326). This was confirmed by screening a rat liver cDNA library in the presence of an anti-50 kDa protein antibody, purified by affinity from an LKM-positive serum. Both constitutive forms of cytochrome P450, belonging to the subfamily IID 1 and 2 (rat db1 and db2), have been identified, as the antigens recognized by the anti-LKM antibody (Gueguen et al., 1988 Exp. Med., 168: 801).

Other studies (Gueguen et al., 1989, Biochem. Biophys. Res. Commun, 159: 542; Zanger et al., 1988., Proc. Natl. Acad. USA, 1988, 27: 8256; Manns et al., 1989 J. Clin. Invest, 83:, 1066) have shown that cytochrome P450 IID6 is a protein recognized in human liver by the anti-LKM antibody. (Gueguen et al., 1989, Biochem. Biophys. Res. Commun, 159: 542; Zanger et al., 1988., Proc. Nati. Acad. USA, 1988, 27: 8256; Manns et al., 1989 J. Clin. Invest., 83:, 1066). Recently a solid-phase immnunoassay for the detection and quantification of LKM autoantibodies has been described (U.S. Pat. No. 5,741,654, Michel et al.) Other tests have therefore been proposed for the detection of autoantibodies, in particular an RIA test (See Clin. Exp. Immunol., 1984 (57); 600–608. Liver-kidney microsomal auto-antibodies are detected by radioimmunoassay and their relation to anti-mitochondial antibodies in inflammatory liver diseases), which h the general disadvantages of RIA tests (especially difficulty of obtaining and handling labelled reagents).

A diagnostic test for AIH has been described which utilizes a fusion protein comprising cytochrome P450 (Gueguan et al., 1989, Biochem. Biophys. Res. Comm., 159 (2), 542–547). A human cytochrome P450 peptide fragment containing an imnmunodominant epitope of cytochrome P450 IID6 binds specifically with the anti-LKM autoantibodies produced during autoimmune hepatitis, and this peptide is the basis for a diagnostic test described in U.S. Pat. No. 5,830,667 issued to F. Alvarez, Nov. 3, 1998. Such an antigen, however, has the disadvantage of also bringing about false positives, especially because of the presence of the associated protein. Thus, one of the greatest difficulties facing those patients suffering from the spectrum of hepatobiliary disorders ranging from PSC to AIH, is not only the lack of curative medical therapy, but is the uncertainty of the curently available methods of clinically diagnosing these disorders.

The pathogenesis of PSC and AIH is probably multifactorial in nature. There are recorded familial clusters of PSC and specific immunogenetic associations with the extended haplotype Al B8 DR3, as well as DR2 and DR52a An infectious etiology is also likely as patients with inherited and acquired immunodeficiency syndromes may also present with an identical choloangiographic appearance of strictures and dilatations within the bile ducts. Recently, evidence for a viral involvement in the pathogenesis of disease has been suggested by the finding that a proportion of patients with PSC have antibody reactivity to retroviral proteins. The importance of this finding has been reinforced by preliminary studies describing the potential involvement of a novel human retrovirus in patients with another idiopathic biliary disease, primary biliary cirrhosis.

3. SUMMARY OF THE INVENTION

The present invention relates, first, to the discovery, identification, and characterization of novel nucleic acid molecules, that are associated with PSC, AIH Crohn's disease and ulcerative colitis. The novel nucleotide sequences of the present invention are retroviral in origin and, are indicative of a PSC associated retrovirus which bears a strong correlation with PSC, AIH, Crohn's disease and ulcerative colitis.

The present inventions encompasses nucleic acid molecules which comprise the following nucleotide sequences: (a) nucleotide sequences comprising the PSC associated retroviral sequences disclosed herein; and (b) nucleotide sequences that encompass portions or fragments of the PSC associated retroviral nucleotides which can be utilized as probes or primers in the methods of the invention for identifying and diagnosing individuals at a risk for, or exhibiting PSC, AIH, Crohn's disease or ulcerative colitis.

The invention also encompasses the expression products of the nucleic acids molecules listed above; i.e., proteins and/or polypeptides that are encoded by the above PSC associated retroviral nucleic acid molecules, or by degenerative, e.g., allelic variants thereof.

The compositions of the present invention further encompass antagonists of the PSC associated retroviral gene products, including small molecules, large molecules, and antibodies, as well as nucleotide sequences that can be used to inhibit PSC associated retroviral gene expression, e.g., antisense, ribozyme molecules, and gene or regulatory sequence replacement constructs.

The present invention relates to therapeutic methods and compositions for treatment and prevention of diseases and disorders associated with the presence of the PSC associated retroviral nucleotides, including but not limited to, PSC, AIH, ulcerative colitis and Crohn's disease. The therapeutic methods and compositions of the present invention are designed to target the PSC associated retroviral nucleotides, such as antisense molecules and ribozymes. The therapeutic methods and compositions of the present invention are also designed to target PSC associated retroviral gene products, including small molecules, large molecules, and antibodies. The present invention further relates to the vaccine formulations based on isolated PSC associated virus particles in an attenuated form and/or PSC associated retroviral gene products for the treatment and/or prevention of disorders associated with the presence of PSC associated retroviral nucleotides.

In addition, the present invention is directed to methods that utilize the nucleotide sequences of the present invention for the diagnostic evaluation, genetic testing and prognosis of PSC associated retroviral infection and/or associated disorders including, (but not limited to PSC, AIH, ulcerative colitis and Crohn's disease. For example, in one embodiment, the invention relates to methods of diagnosing PSC associated retroviral infection and/or associated disorders PSC, AIH, ulcerative colitis and Crohn's disease, wherein such methods comprise measuring PSC associated retroviral gene expression in a patient sample suspected of exhibiting such a disorder. In one embodiment, nucleic acid molecules of the present invention can be used as primers for diagnostic PCR analysis for the identification of PSC associated retroviral nucleotides which correlate with the presence of a PSC associated retrovirus and/or associated disorders PSC, AIH, ulcerative colitis and Crohn's disease. In yet another embodiment, nucleic acid molecules of the present invention can be used as primers for therapeutic PCR analysis in order to monitor the presence of a PSC associated retrovirus in order to determine the effectiveness of a therapeutic protocol.

3.1 Definitions

"Complement" or "tag complement" as used herein in reference to oligonucleotide tags refers to an oligonucleotide to which a oligonucleotide tag specifically hybridizes to form a perfectly matched duplex or triplex. In embodiments where specific hybridization results in a triplex, the oligonucleotide tag may be selected to be either double stranded or single stranded. Thus, where triplexes are formed, the term "complement" is meant to encompass either a double stranded complement of a single stranded oligonucleotide-tag or a single stranded complement of a double stranded oligonucleotide tag.

The term "oligonucleotide" as used herein includes linear oligomers of natural or modified monomers or linkages, including deoxyribonucleosides, ribonucleosides, a-anomeric forms thereof, peptide nucleic acids (PNAs), and the like, that are capable of specifically binding to a target polynucleotide. The specific binding is determined by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides that range in size from a few monomeric units, e.g. 3–4, to several tens of monomeric units. Whenever an oligonucleotide is represented by a sequence of letters, such as "ATGCCTG," it will be understood that the nucleotides are in 5'>3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphorodithioate, phosphoranilidate phosphoramidate, and the like. It is clear to those skilled in the art when oligonucleotides having natural or non-natural nucleotides may be employed, e.g. where processing by enzymes is called for, usually oligonucleotides consisting of natural nucleotides are required. "Perfectly matched" in reference to a duplex means that:the poly- or oligonucleotide strands making up the duplex form a double stranded structure with one other such that every nucleotide in each strand undergoes Watson-Crick basepairing with a nucleotide in the other strand. The term also comprehends the pairing of nucleoside analogs, such as deoxyinosine, nucleosides with 2-aminopurine bases, and the like, that may be employed In reference to a triplex, the term means that the triplex consists of a perfectly matched duplex and a third strand in which every nucleotide undergoes Hoogsteen or reverse Hoogsteen association with a basepair of the perfectly matched duplex. Conversely, a "mismatch" in a duplex between a tag and an oligonucleotide means that a pair or triplet of nucleotides in the duplex or triplex fails to undergo Watson-Crick and/or Hoogsteen and/or reverse Hoogsteen bonding. It also includes known types of modifications, for example, labels which are known in the art, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide.

As used herein, "nucleoside" includes the natural nucleosides, including 2'-deoxy and 2'-hydroxyl forms, e.g. as described in Komberg and Baker, DNA Replication, 2nd Ed (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543–584 (1990), or the like, with the only proviso that they are capable of hybridization. Such analogs include synthetic nucleosides designed to enhance binding properties, reduce degeneracy, increase or decrease specificity, and the like.

As used herein, a polynucleotide "derived from" a designated sequence refers to a subset of the designated sequence of approximately at least about 6 nucleotides, preferably at least about 8 nucleotides, more preferably at least about 1–112 nucleotides, and even more preferably at least about 15–20 nucleotides. "Corresponding" means homologous to or complementary to the designated sequence. Preferably, the sequence of the region from which the polynucleotide is derived is homologous to or complementary to a sequence which is unique to an PSC associated viral genome. More preferably, the derived sequence is homologous or complementary to a sequence that is unique to all or to a majority of PSC associated viral isolates. Whether or not a sequence is unique to the a PSC associated viral genome can be determined by techniques known to those of skill in the art. For example, the sequence can be compared to sequences in databanks, e.g., Genebank, to determine whether it is present in the uninfected host or other organisms. The sequence can also be compared to the known sequences of other viral agents, including retroviruses. The correspondence or non-correspondence of the derived sequence to other sequences can also be determined by hybridization under the appropriate stringency conditions. Hybridization techniques for determining the complementarity of nucleic acid sequences are known in the art, and are discussed infra. See also, for example, Maniatis et al. (1982). In addition, mismatches of duplex polynucleotides formed by hybridization can be determined by known techniques, including for example, digestion with a nuclease such as S1 that specifically digests single-stranded areas in duplex polynucleotides. Regions from which typical DNA sequences, may be "derived" include but are not limited to, for example, regions encoding specific epitopes, as well as non-transcribed and/or non-translated regions.

The derived polynucleotide is not necessarily physically derived from the nucleotide sequence shown, but may be generated in any manner, including for example, chemical synthesis or DNA replication or reverse transcription or transcription. In addition, combinations of regions corresponding to that of the designated sequence may be modified in ways known in the art to be consistent with an intended use.

The term "recombinant polynucleotide" as used herein intends a polynucleotide of genomic, cDNA, semisynthetic, or synthetic origin. The term further intends that the polynucleotide (1) is not associated with all or a portion of a polynucleotide with which it is associated in nature; (2) is linked to a polynucleotide other than that to which it is linked in nature; or (3) does not occur in nature.

As used herein, the "sense strand" of a nucleic acid contains the sequence that has sequence homology to that of mRNA The "anti-sense strand" contains a sequence which is complementary to that of the "sense strand".

The term "primer" as used herein refers to an oligomer which is capable of acting as a point of initiation of synthesis of a polynucleotide strand when placed under appropriate conditions. The primer will be completely or substantially complementary to a region of the polynucleotide strand to be copied. Thus, under conditions conducive to hybridization, the primer will anneal to the complementary region of the analyte strand. Upon addition of suitable reactants, (e.g., a polymerase, nucleotide triphosphates, and the like), the primer is extended by the polymerizing agent to form a copy of the analyte strand. The primer may be single-stranded, or alternatively may be partially or fully double-stranded.

The terms "analyte polynucleotide" and "analyte strand" refer to a single- or double-stranded nucleic acid molecule which is suspected of containing a target sequence, and which may be present in a biological sample. As used herein, the term "oligomer" refers-to primers and to probes. The term oligomer does not connote the size of the molecule.

As used herein, the term "probe" refers to a structure comprised of a polynucleotide which forms a hybrid structure with a target sequence, due to complementarity of at least one sequence in the probe with a sequence in the target region. The polynucleotide regions of probes may be composed of DNA, and/or RNA, and/or synthetic nucleotide analogs. Included within probes are "capture probes" and "label probes". Preferably the probe does not contain a sequence complementary to sequence(s) used to prime the polymerase chain reaction (PCR).

As used herein, the term "target region" refers to a region of the nucleic acid which is to be amplified and/or detected. The term "target sequence" refers to a sequence with which a probe or primer will form a stable hybrid under desired conditions.

As used herein, the term "viral RNA", which includes PSC associated RNA, refers to RNA from the viral genome, fragments thereof, transcripts thereof, and mutant sequences derived therefrom.

As used herein, a "biological sample" refers to a sample of tissue or fluid isolated from an individual. Thus, "biological sample", includes but is not limited to, for example, plasma, serum, spinal fluid, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components).

4. DETAILED DESCRIPTION OF THE DRAWINGS

FIG. 1 Phylogenetic tree of Clustal W alignments using reverse trascriptase pol gene sequences: PBCRV PBC retroviral sequence cloned in our laboratory, SMRV Squirrel monkey retrovirus, MPMV Mason-Pfizer monkey virus, HERVK Human Endogenous retrovirus-K, MIAP Murine intracisternal A-type particle, HRV-5 Human retrovirus 5, PSCRV PSC retroviral sequence cloned in our laboratory, HFV Human foamy retrovirus, HIV Human immunodeficiency virus, MSRV Multiple sclerosis retrovirus, MMLV Murine Moloney leukemia virus, HTLV1 Human T-cell leukemia virus-1, HBV hepatitis B virus.

5. DETAILED DESCRIPTION OF THE INVENTION

The present invention is based on the discovery, identification and characterization of a PSC associated retrovirus isolated from tissue samples of patients with PSC, AIH, ulcerative colitis and Crohn's disease. A pure preparation of virus was obtained from bile samples of patients with Crohn's disease, PSC, ulcerative colitis and AIH. Once the virus was isolated, total RNA was extracted and converted to cDNA using random primers and reverse trascriptase. A novel nucleotide sequence was amplified from the patients tissue sample were identical to each other and has no close homology to known retroviral sequences.

The present invention relates to isolated preparations of a novel retrovirus associated with Crohn's disease, PSC, ulcerative colitis and AIH, herein referred to as "PSC associated retrovirus". The present invention relates to isolated genome of the novel retrovirus and the nucleotide and the nucleic acid molecules encoding said genome. The present invention relates to nucleotide sequences that encompass portions or fragments of the PSC associated retroviral nucleotides which can be utilized as probes or primers in the methods of the invention for identifying and diagnosing individuals at a risk for or exhibiting PSC, AIH, Crohn's disease, and ulcerative colitis.

The present invention encompasses methods for the diagnostic evaluation, and prognostic evaluation of PSC associated retroviral infection and associated disorders including PSC, AIH, ulcerative colitis and Crohn's disease, wherein such methods comprise utilizing the nucleic acid molecules of the present invention to measure levels of PSC associated retroviral nucleotide sequences.

The present invention further provides for diagnostic kits for the practice of such methods.

The present invention relates to therapeutic methods and compositions for treatment and prevention of diseases and disorders related to the infection with the PSC associate retrovirus and/or presence of the PSC associated retroviral nucleotide sequences, including but not limited to, PSC, AIH, ulcerative colitis and Crohn's disease. The therapeutic methods and compositions are designed to target the PSC associated retroviral nucleotides, such as antisense molecules, and ribozymes. The therapeutic methods and compositions of the present invention are also designed to target the PSC associated retroviral gene products, including small molecules, large molecules and antibodies. In particular, the present invention encompasses the use of the isolated PSC associated retrovirus and retroviral gene products to generate antibodies for the detection of the PSC associated retrovirus in tissue samples in diagnostic protocols and/or for formulation into vaccine preparations for the treatment and/or prevention of PSC associated retrovirus infection and related disorders, PSC, AIH, ulcerative colitis and Crohn's disease.

5.1 PSC Associated Retroviral Nucleotides

The retroviral nucleotides of the present invention are described herein. Unless otherwise stated, the term retroviral or viral nucleotides or nucleic acid molecules' refers collectively to the sequences described herein. The novel retroviral nucleotides of the present invention include, but are not limited to, (a) novel clones identified in samples from PSC patients:

```
OB1-DP52r                                                                    (SEQ ID NO: 1)
5'TGGAAGGTGTTACCACAGGGATAAAGTTTCTAATCAATTCACCTATGGTTATATTCATTTATTC

GACTCCTTTCTCTTTATTCCTCACCATTAATTTTCTTGCCCAAGTACATGGATGACCTCCCT3'

OB1-DP54                                                                     (SEQ ID NO: 2)
5'TGGAAGGTGCTGCCACAAGGATAAAGTTTCCAATCAATTCACCTATGGTTATATTCATTTATTC

GACTCCTTTCTCTTTATTCCTCACCATTAATTTTCTTGCCCAAGTACATGGATGACCTCCC3'

OB1-DP55                                                                     (SEQ ID NO: 3)
5'TGGAAGGTGTTGCCACAAGGATAAAGTTTCCAATCAATTCACCTATGGTTATATTCATTTATTC

GACTCCTTTCTCTTTATTCCTCACCATTAATTTTCTTGCCCAAGTACATGGATGACATCA3; and
```

(b) novel clones identified in samples from autoimmune hepatitis patients:

NB6-e27.3r (SEQ ID NO: 4)
5'TTTGGAAGGTGTTGC-CANAGGGATGAAGTTTCCAATCGAATTCACCTATGGTTATATTCATTTA

TTCGACTCCTTTCTCTTTATTCCTCACCATTAATTTTCTTGCCCAAGTACATGGATG3'

NB6-e27.4r (SEQ ID NO: 5)
5'AGG-ATAAAGTTTCCAATCGAATTCACCTATGGTTATATTCATTTATTCGACTC

CTTTCTCTTTATTCCTCACCATTAATTTTCTTGCCCAAGTACATGGAT3'

NB6-e27.5r (SEQ ID NO: 6)
5'CTTTGGAAGGTGTTGCCCCAAGG-ATAAAGTTTCCAATC-AATGCACCTATGGTTATATTCATTTA

TTCGACTCCTTTCTCTTTATTCCTCACCATTAATTTTCTTGCCCAAGTACATGGAT3'

NB6-e27.15r (SEQ ID NO: 7)
5'TTTGGAAGGTGTTGCNNNAGGGAATAAAGTTTCCCAATCGAATTCACCTATGGTTATATTCATTTA

TTCGACTCCTTTCTCTTTATTCCTCACCATTAATTTTCTTGCCCAAGTACATGGA3'

The PSC associated retroviral nucleotide sequences of the present invention include: (a) nucleotide sequences and fragments thereof (e.g. SEQ ID Nos: 1, 2, 3, 4, 5, 6 and 7) that encode a portion of the PSC associated retroviral genome of the present invention; (b) nucleotide sequences that comprise SEQ ID NOS: 1, 2, 3, 4, 5, 6 or 7 that encode a PSC associated retroviral genome or a portion, mutant or allelic variant thereof; (c) nucleotide sequences comprising the novel retroviral sequences disclosed herein that encode retroviral gene products, as well as fragments thereof; and (d) nucleotide sequences (e.g. primers) within SEQ ID NOS. 1, 2, 3, 4, 5, 6 or 7), or a portion thereof, which can be utilized as part of the methods of the invention for identifying and diagnosing individuals at a risk for exhibiting PSC, AIH, Crohn's disease and ulcerative colitis.

The PSC associated retroviral nucleotide sequences of the invention further include: (a) any nucleotide sequence that hybridizes to the complement of a nucleic acid molecule that encodes an PSC associated retroviral gene product under highly stringent conditions, e.g. hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. 1, Green Publishing Associates, Inc., and John Wiley & sons, Inc., New York, at p. 2.10.3). In a preferred embodiment, such nucleic acid molecules encode gene products functionally equivalent to a PSC associated retroviral gene product; and (b) any nucleotide sequence that hybridizes to the complement of a nucleic acid molecule that encodes a PSC associated retroviral gene product under less stringent conditions, such as moderately stringent conditions, e.g., washing in 0.2×SSC/0.1% SDS at 42° C. (Ausubel et al., 1989, sup and which encodes a functionally equivalent PSC associated retroviral gene product. Functional equivalents of PSC associated retroviral nucleotides include naturally occurring PSC associated retroviral nucleic acid molecules present in the same or different species.

Among the nucleic acid molecules of the invention are deoxyoligonucleotides ("oligos") which hybridize under highly or moderately stringent conditions to the PSC associated retroviral nucleic acid molecules described above. Exemplary highly stringent conditions may refer, e.g. to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as antisense molecules, useful, for example, in PSC associated retroviral gene regulation, and/or as antisense primers in amplification reactions of PSC associated retroviral gene nucleic acid sequences. Further, such sequences may be used as part of ribozyme and/or triple helix sequences, also useful for PSC associated retroviral gene regulation. Still further, such molecules may be used as components of diagnostic methods whereby, for example, the presence of a particular PSC associated retroviral nucleic acid molecules involved in a disorder, such as PSC, AIH, Crohn's disease or ulcerative colitis, may be detected.

Fragments of the PSC associated retroviral nucleic acid molecules can be at least 10 nucleotides in length. In alternative embodiments, the fragments can be about 20, 30, 40, 50, 60, 70, 80, 90, 100, 200, 300, 400, 500, 1000, or more nucleotides in length. Alternatively, the fragments can comprise sequences that encode at least 10, 20, 30, 40, 50, 100, or more continuous amino acid residues of the PSC associated retroviral gene products.

The PSC associated retroviral nucleotide sequences of the it invention can be readily obtained, for example, by standard sequencing and the sequence provided herein.

With respect to the cloning of additional allelic variants of the PSC associated retroviral genome gene and homologues from other species (e.g., mouse), the isolated PSC associated retroviral genie sequences disclosed herein may be labeled and used to screen a cDNA library constructed from mRNA obtained from appropriate cells or tissues (e.g., brain and retinal tissues) derived from the organism (e.g., guinea pig, bovine, and mouse) of interest. The hybridization conditions used should generally be of a lower stringency when the cDNA library is derived from an organism different from the type of organism from which the labeled sequence was derived.

Alternatively, the labeled fragment may be used to screen a genomic library derived from the organism of interest, again, using appropriately stringent conditions. Low stringency conditions are well known to those of skill in the art, and will vary predictably depending on the specific organisms from which the library and the labeled sequences are derived For guidance regarding such conditions see, for example, Sambrook, et al., 1989, Molecular Cloning, A Laboratory Manual, Second Edition, Cold Spring Harbor Press, N.Y.; and Ausubel, et al., 1989, Current Protocols in Molecular Biology, Green Publishing Associates and Wiley Interscience, N.Y.

Further, a PSC associated retroviral genome allelic variant may be isolated from, for example, human nucleic acid, by performing PCR using two degenerate oligonucleotide primer pools designed on the basis of nucleotide sequences disclosed herein. The template for the reaction may be cDNA obtained by reverse transcription of mRNA prepared from, for example, human or non-human cell lines or tissue known or suspected to express a retroviral genome allele (such as, for example, livertissue from individuals having PSC, AIH, Crohn's disease or lucerative colitis.

The PCR product may be subcloned and sequenced to ensure that the amplified sequences represent the sequences of a PSC associated retroviral genome nucleic acid sequence. The PCR fragment may then be used to isolate a full length cDNA clone by a variety of methods. For example, the amplified fragment may be labeled and used to screen a bacteriophage cDNA library. Alternatively, the labeled fragment may be used to isolate genomic clones via the screening of a genomic library.

PCR technology and rapid amplification of CDNA ends (RACE) may also be utilized to isolate full length cDNA sequences. In particular the nucleic acids of the present invention may be used to isolate the PSC associated viral genome from patients' samples, infectd biliary epithelial cells, or by screening a full representation of PSC liver cDNA libraries.

In accordance with the present invention, upon identification of retroviral genomic nucleic acid molecules, the presence of retroviral particles may be determined using routine protocols known to those skilled in the art, e.g., co-culture hepatic tissue samples from PSC patients with cultured cells, intra-hepatic biliary epithelial cells, cultured biliary epithelium cells, HepG2, HCC and RH9 lympholoastoid cell lines. Evidence for retroviral infection may be determined by RT-PCR, cell morphology, electron microcopy, and Western blot of virla extracts. RNA derived from filtered use to isolate the viral genome.

Further, accordance with the present invention, RNA may be isolated, following standard procedures, from an appropriate cellular or tissue source (i.e., one known, or suspected, to express the PSC associated retroviral genome, such as, for example, liver tissue samples obtained through biopsy or post-mortem from a subject with PSC). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies that may be used, see e.g., Sambrook et al., 1989, *supra*.

A cDNA of a mutant allelic variant of the PSC associated retroviral genome may be isolated, for example, by using PCR, a technique that is well known to those of skill in the art. In this case, the first cDNA strand maybe synthesized by hybridizing an oligo-dT oligonucleotide to mRNA isolated from tissue known or suspected to be expressed in an individual putatively carrying the mutant PSC associated retroviral allele,! and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant PSC associated retroviral allele to that of the normal PSC retroviral allele, the mutation(s) responsible for the loss or alteration of function of the mutant PSC associated retroviral gene product can be ascertained.

Alternatively, a genomic library can be constructed using DNA obtained from an individual suspected of or known to carry a mutant PSC associated retroviral allele, or a cDNA library can be constructed using RNA from a tissue known, or suspected, to express a mutant PSC associated retroviral allele. An unimpaired PSC associated retroviral genome or any suitable fragment thereof may then be labeled and used as a probe to identify the corresponding mutant PSC associated retroviral allele in such libraries. Clones containing the mutant PSC associated retroviral sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant PSC associated retroviral allele in an individual suspected of or known to carry such a mutant allele. In this manner, gene products made by the putatively mutant tissue may be expressed and screened using standard antibody screening techniques in conjunction with antibodies raised against the normal PSC associated-retroviral gene product, as described, below, in Section 5.3. (For screening techniques, see, for example, Harlow and Lane, eds., 1988, "Antibodies: A Laboratory Manual", Cold Spring Harbor Press, Cold Spring Harbor.)

The invention also includes nucleic acid molecules,- preferably DNA molecules, that are the complements of the nucleotide sequences of the preceding paragraphs.

5.2 Protein Products of the PSC Associates Retroviral Genome

PSC associated retroviral gene products, or peptide fragments thereof, can be prepared for a variety of uses. For example, such gene products, or peptide fragments thereof, can be used for the generation of antibodies, in diagnostic assays, or for the identification of other cellular or extracellular gene products involved in the regulation of disorders, such as PSC, AIH, Crohn's disease and ulcerative colitis.

In addition, PSC associated retroviral genome products may include proteins that represent functionally equivalent gene products. Functionally equivalent gene products may include, for example, gene products encoded by one of the PSC associated retroviral nucleic acid molecules described in Section 5.1, above. In preferred embodiments, such functionally equivalent PSC associated retroviral gene products are naturally occuring gene products. Such an equivalent PSC associated retroviral gene product may contain deletions, including internal deletions, additions, including additions yielding fusion proteins, or substitutions of amino acid residues within and/or adjacent to the amino acid sequence encoded by the PSC associated retroviral gene sequences described, above, in Section 5.1, but that result in a "silent" change, in that the change produces a PSC associated retroviral gene product with the same activity.

Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

5.3 Antibodies to PSC Associated Retroviral Gene Products

Described herein are methods for the production of antibodies capable of specifically recognizing one or more PSC associated retroviral gene product epitopes or epitopes of conserved variants or peptide fragments of the PSC associated retroviral gene products. Further, antibodies that specifically recognize mutant forms of PSC associated retroviral, are encompassed by the invention.

Such antibodies may include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above, including the polyclonal and monoclonal antibodies. Such antibodies may be used, for example, in the detection of a PSC associated retroviral gene product in an biological sample and may, therefore, be utilized as part of a diagnostic or prognostic technique whereby patients may be tested for abnormal levels of PSC associated retroviral gene products, and/or for the presence of abnormal forms of such gene products. Such antibodies may also be utilized in conjunction with, for example, compound screening schemes, for the evaluation of the effect of test compounds on PSC associated retroviral gene product levels and/or activity. Additionally, such antibodies can be used in conjunction with the gene therapy techniques described below, to evaluate the normal and/or engineered PSC associated retroviral genome expressing cells prior to their introduction into the patient.

Anti-PSC associated retroviral gene product antibodies may additionally be used in pharmaceutical formulations and used in methods for the treatment and/or prevention of PSC associated retroviral infection and associated disorders PSC, AIH, Crohn's disease and ulcerative colitis.

For the production of antibodies against a PSC associated retroviral gene product or a PSC associated retrovius various host animals may be immunized by injection with a PSC associated retroviral gene product or PSC associated retroviral particles. Such host animals may include, but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, or an antigenic functional derivative thereof. For the production of polyclonal antibodies, host animals such as those described above, may be immunized by injection with PSC associated retroviral gene product or viral particles supplemented with adjuvants as also described above.

Monoclonal antibodies, which are homogeneous populations of antibodies to a particular antigen, may be obtained by any technique that provides for the production of antibody molecules by continuous cell lines in culture. These include, but are not limited to, the hybridoma technique of Kohler and Milstein, (1975, Nature 256:495–497; and U.S. Pat. No. 4,376,1 10), the human B-cell hybridoma technique (Kosbor et al., 1983, Immunology Today 4:72; Cole et al., 1983, Proc. Nat. Acad. Sci. USA 80:2026–2030), and the EBV-hybridoma technique (Cole et a., 1985, Monoclonal Antibodies And Cancer Therapy, Alan R. Liss, Inc., pp. 77–96). Such antibodies may be of any immunoglobulin class including IgG, IgM,; IgE, IgA, IgD and any subclass thereof. The hybridoma producing the mAb of this invention may be cultivated in vitro or in vivo. Production of high titers of mAbs in-vivo makes this the presently preferred method of production.

In addition, techniques developed for the production of "chimeric antibodies" (Morrison, et al., 1984, Proc. Natl. Acad. Sci., 81:6851–6855; Neuberger, et al., 1984, Nature 312:604–608; Takeda, et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816397, which are incorporated herein by reference in their entirety.)

In addition, techniques have been developed for the production of humanized antibodies. (See, e.g., Queen, U.S. Pat. No. 5,585,089, which is incorporated herein by reference in its entirety.) An immunoglobulin light or heavy chain variable region consists of a "framework" region interrupted by three hypervariable regions, referred to as complementarily determining regions (CDRs). The extent of the framework region and CDRs have been precisely defined (see, "Sequences of Proteins of Immunological Interest", Kabat, E. et al., U.S. Department of Health and Human Services (1983) ). Briefly, humanized antibodies are antibody molecules from non-human species having one or more CDRs from the non-human species and a framework region from a human immunoglobulin molecule.

Alternatively, techniques described for the production of single chain antibodies (U.S. Pat. 4,946,778; Bird, 1988, Science 242:423–426; Huston, et al., 1988, Proc., Natl. Acad. Sci. USA 85:5879–5883; and Ward, et al., 1989, Nature 334:544–546) can be adapted to produce single chain antibodies against PSC associated retroviral particles and PSC associated retroviral gene products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the F(ab')$_2$ fragments, which can be produced by pepsin digestion of the antibody molecule and the Fab fragments, which can be generated by reducing the disulfide bridges of the F(ab')$_2$ fragments. Alternatively, Fab expression libraries may be constructed (Huse, et al., 1989, Science 246:1275–1281) to allow rapid and easy identification of monoclonal Fab fragments with the desired specificity.

5.4. Uses of PSC Associated Retroviral Gene Sequences Gene Products, and Antibodies Described herein are various applications of isolated PSC associated retroviral particles, gene sequences, PSC associated retroviral gene products, including peptide fragments and fusion proteins thereof, and of antibodies directed against PSC associated retroviral gene products and peptide fragments thereof. Such applications include, for example, characterization of the complete genome of the PSC associated retrovirus; identification and characterization of novel retroviruse, prognostic and diagnostic evaluation of an infection by PSC associated retrovirus or associated disorders, PSC AIM, Crohn's disease and ulcerative colitis, and the identification of subjects with a predisposition to such disorders.

Additionally, such applications include methods for the treatment of infection by PSC associated retrovirus or associated disorders, PSC, AIH, Crohn's disease and ulcerative colitis, as described below and for the identification of compounds that modulate the expression of the PSC associated retroviral gene and/or the synthesis or activity of the PSC associated retroviral gene product.

5.5 Diagnosis of PSC Associated Retrovirus and Related Disorders

A variety of methods can be employed for the diagnostic and prognostic evaluation of PSC associated retrovirus infection and related disorders PSC, AIH, Crohn's disease and ulcerative colitis and for the identification of subjects having a predisposition to such disorders.

Such methods may, for example, utilize reagents such as the PSC associated retroviral gene nucleotide sequences described in Sections 5.1, and antibodies directed against PSC associated retroviral gene products, including peptide fragments thereof, as described, above, in Section 5.3. Specifically, such reagents may be used, for example, for.

(1) the detection of the presence of PSC associated retroviral nucleotide sequences;

(2) the detection of presence of PSC associated retroviral gene product.

The detection methods of the present invention can be utilized in pharmacogenetic methods to monitor and to optimize therapeutic drug treatments.

The methods described herein may be performed, for example, by utilizing pre-packaged diagnostic kits comprising at least one specific PSC associated retroviral nucleic acid or anti-PSC associated retroviral gene product antibody reagent described herein, which maybe conveniently used, e.g., in clinical settings, to diagnose patients exhibiting PSC, AIH, Crohn's disease and ulcerative colitis and infection by the PSC associated retrovirus.

5.6 Detection of PSC Associated Retroviral Nucleic Acid Molecules

A variety of methods can be employed to screen for the presence of PSC associated retroviral to detect and/or assay levels of PSC associated retroviral nucleic acid sequences.

PSC associated retroviral nucleic acid sequences may be used; in hybridization or amplification assays of biological samples to detect levels and abnormalities involving PSC associated retroviral genome structure, including point mutations, insertions, deletions, inversions, translocations and chromosomal rearrangements. Such assays may include, but are not limited to, Southern analyses, single-stranded conformational polymorphism analyses (SSCP), and PCR analyses.

Diagnostic methods for the detection of PSC associated retroviral gene-specific mutations can involve for example, contacting and incubating nucleic acids obtained from a sample, e.g., derived from a patient sample or other appropriate cellular source with one or more labeled nucleic acid reagents including recombinant DNA molecules, cloned genes or degenerate variants thereof, such as described in Section 5.1, above, under conditions favorable for the specific annealing of these reagents to their complementary sequences within or flanking the PSC associated retroviral genome. The diagnostic methods of the present invention further encompass contacting and incubating nucleic acids for the detection of single nucleotide mutations or polymorphisms of the PSC associated retroviral genome.

After incubation, all non-annealed nucleic acids are removed from the nucleic acid: PSC associated retroviral molecule hybrid. The presence of nucleic acids that have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described in Section 5.1 are easily removed. Detection of the remaining, annealed, labeled PSC associated retroviral nucleic acid reagents is accomplished using standard techniques well-known to those in the art. The PSC associated retroviral gene sequences to which the nucleic acid reagents have annealed can be compared to the annealing pattern expected from a normal PSC associated retroviral gene sequence in order to determine whether a PSC associated retroviral gene mutation is present.

In a preferred embodiment, PSC associated retroviral mutations or polymorphisms can be detected by using a microassay of PSC associated retroviral nucleic, acid sequences immobilized to a substrate or "gene chip" (see, e.g. Cronin, et al., 1996, Human Mutation 7:244–255).

Alternative diagnostic methods for the detection of PSC associated retroviral gene specific nucleic acid molecules, in patient samples or other appropriate cell sources, may involve their amplification, e.g., by PCR (the experimental embodiment set forth in Mullis, 1987, U.S. Pat. No. 4,683, 202), followed by the analysis of the amplified molecules using techniques well known to those of skill in the art, such as, for example, those listed above.

Those PSC associated retroviral nucleic acid sequences which are preferred for such amplification-related diagnostic screening analyses are oligonucleotide primers which are described in the Working Examples herein.

Additional PSC associated retroviral nucleic acid sequences which are preferred for such amplification-related analyses are those which will detect the presence of an PSC associated retroviral polymorphism. Such polymorphisms include ones which represent mutations associated with an PSC associated retroviral-mediated disorders.

Additionally, well-known genotyping techniques can be performed to identify individuals carrying PSC associated retroviral gene mutations. Such techniques include, for example, the use of restriction fragment length polymorphisms (RFLPs), which involve sequence variations in one of the recognition sites for the specific restriction enzyme used.

Further, improved methods for analyzing DNA polymorphisms, which can be utilized for the identification of PSC associated retroviral gene-specific mutations, have been described that capitalize on the presence of variable numbers of short, tandemly repeated DNA sequences between the restriction enzyme sites. For example, Weber (U.S. Pat. No. 5,075,217) describes a DNA marker based on length polymorphisms in blocks of (dC-dA)n-(dG-dT)n short tandem repeats. The average separation of (dC-dA)n-(dG-dT)n blocks is estimated to be 30,000–60,000 bp. Markers that are so closely spaced exhibit a high frequency co-inheritance, and are extremely useful in the identification of genetic mutations, such as, for example, mutations within the PSC associated retroviral gene, and the diagnosis of diseases and disorders related to PSC associated retroviral mutations.

Also, Caskey et al. (U.S. Pat. No. 5,364,759) describe a DNA profiling assay for detecting short tri and tetra nucleotide repeat sequences. The process includes extracting the DNA of interest, such as the PSC associated retroviral gene, amplifying the extracted DNA, and labelling the repeat sequences to form a genotypic map of the individual's DNA.

Other methods well known in the art may be used to identify single nucleotide polymorphisms (SNPs), including biallelic SNPs or biallelic markers which have two alleles, both of which are present at a fairly high frequency in a population. Conventional techniques for detecting SNPs include, e.g., conventional dot blot analysis, single stranded conformational polymorphism (SSCP) analysis(see, e.g., Orita et al, 1989, *Proc. Natl Acad. Sci. USA* 86:2766–2770), denaturing gradient gel electrophoresis (DGGE), heteroduplex analysis, mismatch cleavage detection, and other routine techniques well known in the art (see, e.g., Sheffield et al., 1989, *Proc. Natl. Acad. Sci*. 86:5855–5892; Grompe, 1993, *Nature Genetics* 5:111–117). Alternative, preferred methods of detecting and mapping SNPs involve microsequencing techniques wherein an SNP site in a target DNA is detecting by a single nucleotide primer extension reaction (see, e.g., Goelet et al., PCT Publication No. WO92/15712; Mundy, U.S. Pat. No. 4,656,127; Vary and Diamond, U.S. Pat. No. 4,851,331; Cohen et al., PCT Publication No. WO91/02087; Chee et al, PCT Publication No. WO95/11995; Landegren et al., 1988, *Science* 241:1077–1080; Nicerson et al., 1990, *Proc. Natl. Acad. Sci. U.S.A*. 87:8923–8927; Pastinen et al.,1997, *Genome Res*. 7:606–614; Pastinen et al., 1996, *Clin. Chem*. 42:1391–1397; Jalanko et al, 1992, *Clin. Chem*. 38:3943; Shumaker et al., 1996, *Hum. Mutation* 7:346–354; Caskey et al., PCT Publication No. WO 95/00669).

The level of PSC associated retroviral gene expression can also be assayed. For example, RNA from a cell type or tissue known, or suspected, to express the PSC associated retroviral gene, such as bile duct or liver tissue, may be isolated and tested utilizing hybridization or PCR techniques such as are described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the PSC associated retroviral gene. Such analyses may reveal both quantitative and qualitative aspects of the expression pattern of the PSC associated retroviral gene, including activation or inactivation of PSC associated retroviral gene expression.

In one embodiment of such a detection scheme, a cDNA molecule is synthesized from an RNA molecule of interest (e.g., by reverse transcription of the RNA molecule into cDNA). A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the PSC associated retroviral gene nucleic acid reagents described in Section 5.1. The preferred lengths of such nucleic acid reagents are at least 9–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Additionally, it is possible to perform such PSC associated retroviral gene expression assays "in situ", i.e., directly upon tissue sections. (fixed and/or frozen) of patient tissue obtained from biopsies or resections, such that no nucleic acid purification is necessary. Nucleic acid reagents such as those described in Section 5.1 may be used as probes and/or primers for such in situ procedures (see, for example, Nuovo, G. J., 1992, "PCR In Situ Hybridization: Protocols And Applications", Raven Press, NY).

Alternatively, if a sufficient quantity of the appropriate cells can be obtained, standard Northern analysis can be performed to determine the level of mRNA expression of the PSC associated retroviral gene.

1 5.7 Inhibitory Antisense, Ribozyme and Triple Helix Approaches

In another embodiment, symptoms of PSC associated retroviral-mediated disorders may be ameliorated by decreasing the level of PSC associated retroviral gene expression and/or PSC associated retroviral gene product activity by using PSC associated retroviral gene sequences in conjunction with well-known antisense, gene "knockout," ribozyme and/or triple helix methods to decrease the level of PSC associated retroviral gene expression. Among the compounds that may exhibit the ability to modulate the activity, expression or synthesis of the PSC associated retroviral gene, including the ability to ameliorate the symptoms of a PSC associated retroviral-mediated disorder, are antisense, ribozyme, and triple helix molecules. Such molecules may be designed to reduce or inhibit either unimpaired, or if appropriate, mutant target gene activity. Techniques for the production and use of such molecules are well known to those of skill in the art.

Antisense RNA and DNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary-target gene mRNA transcripts and prevent translation. Absolute complementarily, although preferred, is not required.

A sequence "complementary" to a portion of an RNA, as referred to herein, means a sequence having sufficient complementarily to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

In one embodiment, oligonucleotides complementary to non-coding regions of the PSC associated retroviral gene could be used in an antisense approach to inhibit translation of endogenous PSC associated retroviral mRNA. Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and nonspecific biological effects of oligonucleotides. It is also preferred that these studies compare levels of the target RNA or protein with that of an internal control RNA or protein Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger, et al., 1989, Proc. Natl. Acad. Sci. U.S.A. 86:6553–6556; Lemaitre, et al., 1987, Proc. Natl. Acad. Sci. U.S A. 84:648–652; PCT Publication No. WO88/09810, published Dec. 15, 1988) or the blood-brain barrier (see, e.g. PCT Publication No. WO89/10134, published Apr. 25 1988), hybridization-triggered cleavage agents (see, e.g., Krol et al., 1988, BioTechniques 6:958–976) or intercalating agents (see, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group-including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-edimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier, et al., 1987, Nucl. Acids Res. 15:6625–6641). The oligonucleotide is a 2'-0-methylribonucleotide (Inoue, et al., 1987, Nucl. Acids Res. 15:6131–6148), or a chimeric RNA-DNA analogue (Inoue, et al., 1987, FEBS Lett. 215:327–330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein, et al. (1988, Nucl. Acids Res. 16:3209), methylphosphonate oligonucleotides can be prepared by use of controlled pore glass polymer supports (Sarin, et al.,. 1988, Proc. Natl. Acad. Sci. U.S.A 85:7448–7451) etc.

While antisense nucleotides complementary to the target gene coding region sequence could be used, those complementary to the transcribed, untranslated region are most preferred.

Antisense molecules should be delivered to cells that express the target gene in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced e.g., such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamanoto, et al., 1980, Cell 22:787–797), the herpes thymidine kinase promoter (Wagner, et al., 1981, Proc. Natl. Acad. Sci. U.S.A. 78:11–1445), the regulatory sequences of the metalothionein gene (Brinster, et al., 1982, Nature 296:39–42), etc. Any type of plasmid, cosmid, YAC or viral vector can be used to prepare the recombinant DNA construct which can be introduced directly into the tissue site. Alternatively, viral vectors can be used that selectively infect the desired tissue, in which case administration may be accomplished by another route (e.g., systemically).

Ribozyme molecules designed to catalytically cleave target gene mRNA transcripts can also be used to prevent translation of target gene mRNA and, therefore, expression of target gene product. (See, e g., PCT International Publication WO90/11364, published Oct. 4, 1990; Sarver, et al., 1990, Science 247, 1222–1225).

Ribozymes are enzymatic RNA molecules capable of catalyzing the specific cleavage of RNA. (For a review, see Rossi, 1994, Current Biology 4:469471). The mechanism of ribozyme action involves sequence specific hybridization of the ribozyme molecule to complementary target RNA, followed by an endonucleolytic cleavage event. The composition of ribozyme molecules must include one or more sequences complementary to the target gene RNA, and must include the well kown catalytic sequence responsible for mRNA cleavage. For this sequence, see, e.g., U.S. Pat. No. 5,093,246, which is incorporated herein by reference in its entirety.

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Myers, 1995, *Molecular Biology and Biotechnology: A Comprehensive Desk Reference*, VCH Publishers, New York, (see especially FIG. 4, page 833) and in Haseloff and Gerlach, 1988, Nature, 334:585–591, which is incorporated herein by reference in its entirety.

Preferably the ribozyme is engineered so that the cleavage recognition site is located near the 5' end of the target gene mRNA, i.e., to increase efficiency and minimize the intracellular accumulation of non-functional mRNA transcripts.

The ribozymes of the present invention also include RNA endoribonucleases (hereinafter "Cech-type ribozymes") such as the one that occurs naturally in *Tetrahymena thermophila* (known as the IVS, or L-19 IVS RNA) and that has been extensively described by Thomas Cech and collaborators (Zaug, et al.,1984, Science, 224:574–578; Zaug and Cech, 1986, Science, 231:47075;Zaug, et al., 1986,Nature, 324:429–433; published International patent application No. WO 88/04300 by University Patents Inc.; Been and Cech, 1986, Cell, 47:207–216). The Cech-type ribozymes have an eight base pair active site which hybridizes to a target-RNA sequence whereafter cleavage of the target RNA takes place. The invention encompasses those Cech-type ribozymes which target eight base-pair active site sequences that are present in the target gene.

As in the antisense approach, the ribozymes can be composed of modified oligonucleotides (e.g., for improved stability, targeting, etc.) and should be delivered to cells that express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target gene messages and inhibit translation. Because ribozymes unlike antisense molecules, are catalytic, a lower intracellular concentration is required for efficiency.

Endogenous target gene expression can also be reduced by inactivating or "knocking out" the target gene or its promoter using targeted homologous recombination (e.g., see Smithies, et al, 1985, Nature 317:230–234; Thomas and Capecchi, 1987, Cell 51:503–12; Thompson, et at., 1989, Cell 5:313–321; each of which is incorporated by reference herein in its entirety). For example, a mutant, non-functional target gene (or a completely unrelated DNA sequence) flanked by DNA homologous to the endogenous target gene (either the coding regions or regulatory regions, of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene (e.g., see Thomas and Capecchi, 1987 and Thompson, 1989, *supra*). However this approach can be adapted for :use in humans provided the recombinant DNA constructs ant directly administered or targeted to the required site in vivo using appropriate viral vectors.

Alternatively, endogenous target gene expression can be reduced by targeting deoxyribonucleotide sequences complementary to the regulatory region of the target gene (i.e., the target gene promoter and/or enhancers) to form triple helical structures that prevent transcription of the target gene in target cells in the body. (See generally, Helene, 1991, Anticancer Drug Des., 6(6):569–584; Helene, et al., 1992, Ann. N.Y. Acad. Sci., 660:27–36; and Maher, 1992, Bioassays 14(12):807–815).

Nucleic acid molecules to be used;in triplex helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC$^+$ triplets across the three associated strands of the resulting triple helix. The pyrimidine-rich molecules provide base complementarily to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'–5' manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix) and/or translation (antisense, ribozyme) of mRNA produced by normal target gene alleles that the possibility ma y arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may, be introduced into cells via gene therapy methods such as those described, below, in Section 5.9.2 that do not contain sequences susceptible to whatever antisense, ribozyme, or triple helix treatments are being utilized Alternatively, in instances whereby the target gene encodes an extracellular protein, it may be preferable to co-administer normal target gene protein in order to maintain the requisite level of target gene activity.

Anti-sense RNA and DNA, ribozyme, and triple helix molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used; can be introduced stably into cell lines.

5.8 Pharmaceutical Preparations and Methods of Administration

The compounds that are determined to affect PSC associated retroviral gene expression or gene product activity can be administered to a patient at therapeutically effective doses to treat or ameliorate a PSC associated retroviral-mediated disorder. A therapeutically effective dose refers to that amount of the compound sufficient to result in amelioration of symptoms of such a disorder.

5.8.1 Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED5_0$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to unnifected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

5.8.2 Formulations and Use.

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

5.9 Vaccine Formulations and Methods of Administration

The PSC associated virus in an attenuated form and PSC associated virus gene products have use in vaccine preparations and in immunoassays, e.g., to detect or measure in a sample of body fluid from a vaccinated subject the presence of antibodies to the antigen, and thus to diagnose infection and/or to monitor immune response of the subject subsequent to vaccination.

The preparation of vaccines containing an immunogenic polypeptide as the active ingredient is known to one skilled in the art.

5.9.1 Determination of Vaccine Efficacy

The immunopotency of the PSC associated virus in an attenuated form and PSC associated virus gene products can be determined by monitoring the immune response in test animals following immunization with the antigen, or by use of any immunoassay known in the art. Generation of a humoral (antibody) response and/or cell-mediated immunity, may be taken as an indication of an immune response. Test animals may include mice, hamsters, dogs, cats, monkeys, rabbits, chimpanzees, etc., and eventually human subjects.

Methods of introducing the vaccine may include oral, intracerebral, intradermal, intramuscular, intraperitoneal, intravenous, subcutaneous, intranasal or any other standard routes of immunization: The immune response of the test subjects can be analyzed by various approaches such as: the reactivity of the resultant immune serum to the antigen, as assayed by known techniques, e.g., immunosorbant assay (ELISA), immunoblots, radioimmunoprecipitations, etc., or in the case where the antigen displays antigenicity or immunogenicity, by protection of the immunized host firm infection by the PSC associated retrovinus and/or attenuation of symptoms due to infection in the immunized host.

As one example of suitable animal testing of a vaccine, the vaccine of the invention may be tested in rabbits for the ability to induce an antibody response to the antigen. Male specific-pathogen-free (SPF) young adult New Zealand White rabbits-may be used. The test group each receives a fixed concentration of the vaccine. A control group receives an injection of 1 mM Tris-HCl pH 9.0 without the antigen.

Blood samples may be drawn from the rabbits every one or two weeks, and serum analyzed for antibodies to the viral protein. The presence of antibodies specific for the antigen may be assayed, e.g., using an ELISA.

5.9.2 Vaccine Formulations

Suitable preparations of such vaccines include injectables, either as liquid solutions or suspensions; solid forms suitable for solution in, suspension in, liquid prior to injection, may also be prepared. The preparation may also be emulsified, or the polypeptides encapsulated in liposomes the active immunogenic ingredients are often mixed with excipients which are pharmaceutically acceptable and compatible with the active ingredient. Suitable excipients are, for example, water saline, dextrose, glycerol, ethanol, or the like and combinations thereof. In addition, if desired, the vaccine preparation may also include minor amounts of auxiliary substances such as wetting or emulsifying agents, pH buffering agents, and/or adjuvants which enhance the effectiveness of the vaccine.

In one embodiment of the invention, recombinant vaccines may be formulated which express the PSC associated retroviral nucleic acid molecules of the present invention. In yet another embodiment, vaccines may be formulated which comprise the isolated PSC associated vetrovirus which has been formulated using conventional techniques to "kill" or attenuate the virus. Such techniques include heat inactivation, or treatment with formalin, formaldehyde or β-propiolactone.

Examples of adjuvants which may be effective, include, but are not limited to: aluminum hydroxide, N-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxyphosphoryloxy)-ethylamine.

The effectiveness of an adjuvant may be determined by measuring the induction of antibodies directed against an immunogenic polypeptide containing a viral polypeptide epitope, the antibodies resulting from administration of this polypeptide in vaccines which are also comprised of the various adjuvants.

The polypeptides may be formulated into the vaccine as neutral or salt forms. Pharmaceutically acceptable salts include the acid addition salts (formed with free amino groups of the peptide) and which are formed with inorganic acids, such as, for example, hydrochloric or phosphoric acids, or organic acids such as acetic, oxalic, tartaric, maleic, and the like. Salts formed with free carboxyl groups may also be derived from inorganic bases, such as, for example, sodium potassium, ammonium, calcium, or ferric hydroxides, and such organic bases as isopropylamine, trirethylamine, 2-ethylamino ethanol, histidine, procaine and the like.

The vaccines of the invention may be multivalent or univalent. Multivalent vaccines are made from recombinant viruses that direct the expression of more than one antigen.

Many methods may be used to introduce the vaccine formulations of the invention; these include but are not limited to oral, intradermal, intramuscular, intraperitoneal, intravenous, subcutaneous, intranasal routes, and via scarification (scratching through the top layers of skin, e.g., using a bifurcated needle).

The patient to which the vaccine is administered is preferably a mammal, most preferably a human, but can also be a nonhuman animal including but not limited to cows, horses, sheep, pigs, fowl (e.g., chickens), goats, cats, dogs, hamsters, mice and rats.

The vaccine formulations of the invention comprise an effective immunizing amount of the viral protein and a pharmaceutically acceptable carrier or excipient. Vaccine preparations comprise an effective immunizing amount of one or more antigens and a pharmaceutically acceptable carrier or excipient. Pharmaceutically acceptable carriers are well known in the art and include but are not limited to saline, buffered saline, dextrose, water, glycerol, sterile isotonic aqueous buffer, and combinations thereof. One example of such an acceptable carrier is a physiologically balanced culture medium containing one or more stabilizing agents such as stabilized, hydrolyzed proteins, lactose, etc. The carrier is preferably sterile. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

Generally, the ingredients are supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile diluent can be provided'so that the ingredients may be mixed prior to administration.

The precise dose of vaccine preparation to be employed in the formulation will also depend on the route of administration, and the nature of the patient, and should be, decided according to the judgment of the practitioner and each patient's circumstances according to standard clinical techniques. An effective immunizing amount is that amount sufficient to produce an immune response to the antigen in the host to which the vaccine preparation is administered.

Use of purified antigens as vaccine preparations can be carried out by standard methods. For example, the purified protein(s) should be adjusted to an appropriate concentration, formulated with any suitable vaccine adjuvant and packaged for use. Suitable adjuvants may include, but are not limited to: mineral gels, e.g., aluminum hydroxide; surface active substances such as lysolecithin, pluronic polyols; polyanions; peptides; oil emulsions; alum, and MDP. The immnunogen may also be incorporated into liposomes, or conjugated to polysaccharides and/or other polymers for use in a vaccine formulation. In instances where the recombinant antigen is a hapten, i.e., a molecule that is antigenic in that it can react selectively with cognate antibodies, but not immunogenic in that it cannot elicit an immune response, the hapten may be covalently bound to a carrier or immunogenic molecule; for instance, a large protein such as serum albumin will confer immunogenicity to the hapten coupled to it. The hapten-carrier may be formulated for use as a vaccine.

Effective doses (immunizing amounts) of the vaccines of the invention may also be extrapolated from dose-response curves derived from animal model test systems.

The invention also provides a pharmaceutical pack or kit comprising one or more containers comprising one or more of the ingredients of the vaccine formulations of the invention. Associated with such container(s) can be a notice in the form prescribed by a governmental agency regulating the manufacture, use or sale of pharmaceuticals or biological products, which notice reflects approval by the agency of manufacture, use or sale for human administration.

The present invention thus provides a method of immunizing an animal, or treating or preventing various diseases or disorders in an animal, comprising administering to the animal an effective immunizing dose of a vaccine of the present invention.

6. EXAMPLES

6.1 Identification of Novel Retroviral Pol Sequences

Bile samples from patients with Inflammatory Bowel Disease (IBD) and control patients undergoing endoscopic retrograde cholangiopancreatography (ERCP) were prospectively collected for study. Two bile samples from a patient with Crohn's disease and PSC and another subject with ulcerative colitis and AIH were processed within 4 to 6 hours of collection. In order to isolate a pure preparation of the putative "retrovirus" from each sample, cellular debris was removed by centrifugation and the supernatant was removed.

Once a "viral pellet" had been derived by ultracentrifugation, total RNA was extracted and converted to cDNA using random primers and reverse transcriptase (RT). Modified consensus primers initially reported by Rush et al to amplify the RT gene of all known retroviruses were then used to amplify a portion of the putative novel retrovirus. Novel nucleotide sequences were amplified from the bile of both patients that shared no close homology to known retroviral sequences. However, both amplified nucleotide sequences were nearly identical to each other.

PCR primers from the novel sequence were constructed using MacVector™ 6.0. These primers were subsequently used to perform RT-PCR and PCR studies on nucleic acid extracted from serum and hepatic samples of patients with various forms of chronic liver disease. In these studies, patients with PSC and AIH were found to have the novel PSC pol sequence whereas the sequence was rarely detected in control. Subsequently, a hepatic cDNA library was constructed from 2 PSC patients with RT-PCR evidence of the novel clone within the liver. This PSC hepatic cDNA library is Genetrapper™ by Gibco BRL using oligonucleotide primers complementary to the novel PSC pol sequence.

RNA extraction and cDNA synthesis of virus preparation from bile samples. PCR amplification of cDNA was carried out using degenerate oligonucleotide primers complementary to conserved region of retroviral reverse transcriptase gene. The PCR products were cloned and sequenced as described herein. Blast search analysis of nucleotide sequences and selection of novel clone repeatedly observed in PSC bile was carried out. Oligonucleotide primers complementary to the sequence of the novel PSC pol clone were synthesized and used in PCR and RT-PCR studies of liver and serum samples derived from patients with various liver diseases. PCR amplification of AIH bile cDNA using degenerate retroviral pol oligonucleotide primers was also conducted. Novel clones with near identity to PSC pol clone were identified. Hepatic cDNA library from 2 PSC patients with demonstrable RT-PCR evidence of novel clone in their samples were constructed and screened by Genetrapper™ (Gibco BRL) using oligonucleotide primers complementary to novel clone.

Materials and Methods

1. Isolation of cDNA from Virus Preparation of Bile Samples

Three fresh bile specimens were used for virus preps using protocol 1. Sample 1 contained about 8 ml of fresh bile from a PSC patient (55 year old female) Sample 2 contained about 6 ml of bile from a PBC patient (42 year old female) Sample 3 contained about 11 ml of fresh bile from a patient with choledocholithiasis (42 year old female).

Protocol 1: Virus Preparation and RNA Extraction

The bile samples were centrifuged at 2,500 rpm (600 gm) for 20 min at 4° C. to remove the cell debris. The supernatant was transferred to a clean ultracentrifuge tube and the tubes were balanced with a solution contained 50 mM Tris-HCl, pH 8.0/100 mM NaCl/1 mM EDTA. After centrifuge at 9,000 rpm with SW28 Rotor for 25 min at 4° C., the supernatant was transferred to a second ultracentrifuge and centrifuged at 28,000 rpm for 4.5 hours with the same rotor.

The pellet was suspended with 150 ul DNAse solution (RNAse free DNAse 5 ul/RNasin 0.2 ul/ 10 mg/ml yeast tRNA 1 ul) and digested at RT for 20 min. 50 ul of "proteinase K solution" was added, containing 1 ul of 10 mg/ml Proteinase k and 0.5 ul of 20% SDS, then incubated at 55° C. for 20 min;

600 ul Trizol LS solution was added to each tube and mixed well. After 10 min at RT 160 ul of Chloroform was added and the tubes vigorously shaken by hand for 15 seconds. After incubation at RT for 5 min, the tubes were centrifuged at 12,000 gm for 15 min at 4° C. The colorless upper aqueous phase was transferred to a clean tube and the RNA was precipitated overnight with 0.4 ml of isopropyl alcohol at −70° C. The tubes were centrifuged at 12,000 gm at 4° C. next morning after warming up to RT for 5–10 min. 75% ethanol in the DEPC water was layered onto the pellet and the tube was centrifuged 7,500 gm twice to wash the RNA.

The pellet was air dried and dissolved in 20 ul of RNAse free water. Immediately after this step, the RNA was reverse transcribed to cDNA cDNA Synthesis of RNA Extracted from Billary Virus Preparation The RNA extracted from the 3 bile samples was reverse transcribed to cDNA Protocol 2: cDNA Synthesis 3.8 ul of 6 mers random primer solution (0.5 ul of 20 uM primer/0.3 ul of RNAsin/3 ul of RNAse free water ) were mixed with 9 ul of RNA extracts from bile. The RNA was denatured at 75° C. for 10 min with the random primers and chilled on ice for 2–3 min. 7.2 ul of M-MLV reaction mix (4 ul of 5× 1st strain buffer/2 ul of 100 mM DTT/0.8 ul M-MLV reverse transcriptase/0.4 ul of 25 mM dNTPs) was added to the tube, mixed well, centrifuged briefly, and incubated at 37° C. for 1 hour;

The enzyme was inactivated for 5 min at 95° C. and the cDNA was stored at −20° C.

2. PCR Amplification of Conserved Retroviral Pol Gene

The 3 bile cDNA samples (protocol 2), and 4 total hepatic cDNA samples from 1 healthy individual, 1 sarcoid patient, 1 PSC patient, and 1 patient with giant cell hepatitis (GCH), were used as substrate for the PCR amplification of the retroviral pol gene. This highly conserved region of the reverse transcriptase gene was amplified using a modification of the oligonucleotide primers originally reported by Shih and colleagues. Using this protocol, the majority of known exogenous and endogenous retroviral pol genes can be amplified.

Retroviral pol gene primer sequences
P976-3 sense     5'-TGGAAIGTIYTRCCMCARGG-3'
P976-2 antisense     5'-IIIIADRTCATCCATRI-3'
Protocol 3: PCR amplification
PCR recipe 5 ul of 10 X Sigma PCR buffer without magnesium
  5 ul of 25 mM Sigma MgCl/0.4 ul of 25 mM dNTPs
  1 ul of 20 uM p976-2 and 1 ul of 20 uM p976-3
  0.5 ul (1 unit) of Sigma Taq polymerase
  1 ul of cDNA and 35.1 ul of water 50 ul total reaction volume
PCR conditions Denature at 94° C. 2 min
5 cycles of 94° C. 10 seconds
58° C. 10 seconds
7° C. 10 seconds with 1° C. reduction in the annealing temperature per cycle 25 cycles of 94° C. 10 seconds
5° C. 10 seconds
7° C. 10 seconds
Final cycle of 7° C. 10 min.

TABLE 1

PCR amplification of liver and bile cDNA using RV pol primers

| Samples | Patients diagnosis | PCR product |
|---|---|---|
| 298 | Healthy liver | 0 |
| 299 | sarcoidosis liver | 0 |
| 300 | ps C liver | 0 |
| 301 | GCH liver | 0 |
| 0B1 | ps C bile | 0 |
| 0B2 | PBC bile | — |
| OB3 | Cholelithiasis | — |

The 126 bp DNA amplified fragment was identified after electrophoresis on a 3% agarose gel by ethidium bromide staining from all hepatic cDNA samples and the PSC cDNA bile sample (see Table 1 for results ). Each product was purified from the gel by Qiagen gel extraction kit and cloned using the pCR TOPO TA™ cloning kit (Invitrogen).

3. Cloning and Sequencing of PCR Products

Protocol 4: Cloning and Sequencing

Five products were cloned from the PCR studies using cDNA from healthy liver, sarcoid liver, PSC liver, GCH liver and PSC bile. These amplicons were cloned into the Intvitrogen pCR®II-Topo vector following the instructions of the manufacturer. The positive clones were screened by using PCR amplification with a primer pair flanking the polylinker region of the vector at the 17 and reverse M13 sites. Clones with a molecular weight of 336 bp observed on agarose gel were considered to have the 126 bp retroviral pol insert.

The positive clones were grown in LB broth with kanamycin and the plasmid DNA was extracted by using Bio101 RPM Mini-prep kit according the manufacturer's guide. The clones were sequenced by using USB T7 polymerase version 2 kit with the M13 primer.

TABLE 2

Screening of plasmid for evidence of cloned products.

| Samples | plasmids screened | plasmids with cloned inserts |
|---|---|---|
| Healthy liver | 10 | 9 |
| Sarcoid liver | 10 | 4 |
| ps C liver | 10 | 6 |
| Giant Cell Hepatitis liver | 10 | 7 |
| ps C bile | 6 | 3 |

4. Blast Search Analysis of Nucleotide Sequences

Sequences were assessed using AssemblyLign™ (Oxford Molecular Group) to group similar sequences and all near identical clones were analyzed by blast search together. Each sequence was submitted for nucleotide and translated protein search of NCBI databases using the Blastn and Blastx search algorithm. Human endogenous retroviral (HERV) sequences were found in the hepatic cDNA from all clones assessed. However, all three sequences derived from the PSC bile cDNA shared 98% homology on the nucleotide level and were found to be novel sequences by both blastn and blastx searches (table 3).

TABLE 3

Novel clones identified in PSC bile.

OB1-DP52r
TGGAAGGTGTTACCACAGGGATAAAGTTTCTAATCAATTCACCTATGGTT

ATATTCATTTATTCGACTCCTTTCTCTTTATTCCTCACCATTAATTTTCT

TGCCCAAGTACATGGATGACCTCCC

OB1-DP54
TGGAAGGTGCTGCCACAAGGATAAAGTTTCCAATCAATTCACCTATGGTT

ATATTCATTTATTCGACTCCTTTCTCTTTATTCCTCACCATTAATTTTCT

TGCCCAAGTACATGGATGACCTCCC

OB1-DP55
TGGAAGGTGTTGCCACAAGGATAAAGTTTCCAATCAATTCACCTATGGTT

ATATTCATTTATTCGACTCCTTTCTCTTTATTCCTCACCATTAATTTTCT

TGCCCAAGTACATGGATGACATCA

Synthesis of Primers Complementary to Novel PSC Clone

Oligonucleotide primers were selected from OB-1 DP54 using MacVecor™ 6.0 software (Kodak).

PSC primer and probe sequences

```
Sense      5'-GTGCTGCCACAAGGATAAAGTTTC-3'
Antisense  5'-GGGAGGTCATCCATGTACTTGG-3'
Probe      5'-CGACTCCTTTCTCTTTATTCCTCAC-3'
```

5. PCR Studies of Liver and Serum Samples Using PSC Pol Primers

Clinical Specimens

The RNA was extracted from serum and bile (see table 5) and reverse transcribed to cDNA as described previously (protocol 2) with M-MLV reverse transcriptase using 6 mers as random primers. The PCR was performed using the following parameters:

TABLE 4

PCR and Southern blot results using ps C primers and probe

| Sample No. | Diagnosis | Material | PCR result | Hybridization |
|---|---|---|---|---|
| S1 | ps C | Serum | − | − |
| S2 | ps C | Serum | − | 0 |
| S3 | ps C | Serum | − | 0 |
| S4 | ps C | Serum | − | 0 |
| S5 | ps C | Serum | − | 0 |
| S6 | ps C | Serum | − | 0 |
| N1 | r/o Lyme's disease | Serum | − | − |
| N2 | Healthy volunteer | Serum | − | 0 |
| OB1 | ps C | Bile | + | 0 |
| OB2 | PBC | Bile | − | − |
| OB3 | Cholelithiasis | Bile | − | − |
| B1 | ps C | Bile | − | − |
| B2 | healthy volunteer | Bile | − | − |
| B3 | Pancreatic Mass | Bile | − | − |
| B4 | Carcinoma Pancreas | Bile | − | − |
| Neg | Control | Water | − | − |

The PCR products were separated on a 3% of agarose gel and transferred to a nylon membrane. The membrane was hybridized with PSC internal oligo probe (protocol 5).

PCR conditions
Denature at        94° C. 3 min
1 cycle of         45° C. 1 min
                   72° C. 1 min
25 cycles of       94° C. 1 min
                   45° C. 40 seconds
                   72° C. 45 seconds
Final cycle of     72° C. 5 min.
Identification of PCR products Protocol 5: Southern Blot and Hybridization The PCR products were separated on the 3% agarose gel and transferred to a Genescreen nylon membrane (Dupont) overnight in an alkali buffer containing 1.5 M NaCl and 0.5 M NaOH. The membranes were neutralized in Sigma neutralizing buffer and the PCR products were crosslinked to the membrane by Stratagene crosslinker Program C-L. The PSC internal oligoprobe was labeled with $p[^{32}1]$ by polynucleotide kinase and hybridized to the membrane at 42° C. overnight in 20% formamide (Sigma). The membranes were washed using 2×SSC/0.1% SDS for 10 min at RT, 1×SSC/0.1%SDS, 10 min twice, then 0.5×SSC/0.1/0.1% SDS 10 min twice at RT. The membrane exposed to Hyperfilm overnight at −70° C.

Further PCR and RT-PCR studies were performed on nucleic acids extracted from serum, liver, colon and bile to assess the prevalence of detection of the PSC pol sequence. These studies were conducted in a blinded fashion where the investigator was not aware of the relevant diagnoses for all the samples. The results recorded are derived from amplification and Southern blot analysis using the PSC pol primers and probe.

TABLE 5

The Detection Rate of Potential ps C Related Viral cDNA Fragment in Patients with Liver Diseases by RT-PCR and Hybridization

| Category | n | Positive | Percentage |
|---|---|---|---|
| Liver cDNA | | | |
| ps C | 12 | 9 | 75% |
| Cryptogenic cirrhosis | 5 | 4 | 80% |
| AIH | 5 | 1 | 20.0% |
| BA | 3 | 1 | 33.3% |
| Sarcoid | 2 | 1 | 50% |
| Healthy | 3 | 0 | 0% |
| EtOH | 1 | 1 | 100% |
| PBC | 15 | 0 | 0% |
| Total | 46 | 17 | 37.0% |
| Colon cDNA | | | |
| Crohn's | 2 | 1 | 50% |
| UC | 1 | 1 | 100% |
| Total | 3 | 2 | 66.7% |
| Bile cDNA | | | |
| ps C | 25 | 18 | 72.0% |
| Cryptogenic cirrhosis | 3 | 2 | 67% |
| AIH | 5 | 1 | 20.0% |
| PBC | 19 | 5 | 26.3% |
| ALD | 6 | 1 | 17% |
| Gall Stones | 2 | 0 | 0% |
| Healthy | 1 | 0 | 0% |
| Pancreatic Cancer | 2 | 1 | 50% |
| BA | 1 | 0 | 0% |

TABLE 5-continued

The Detection Rate of Potential ps C Related Viral cDNA Fragment in Patients with Liver Diseases by RT-PCR and Hybridization

| Category | n | Positive | Percentage |
|---|---|---|---|
| Sarcoid | 1 | 0 | 0% |
| Fulminant Hepatitis | 1 | 0 | 0% |
| TPN | 1 | 1 | 100% |
| Total | 68 | 29 | 42.6% |
| Serum cDNA | | | |
| ps C | 5 | 4 | 80.0% |
| Cryptogenic cirrhosis | 1 | 1 | 100% |
| AIH | 2 | 2 | 100% |
| ALD | 5 | 0 | 0% |
| PBC | 20 | 3 | 15.0% |
| Healthy | 2 | 1 | 50.0% |
| Hyperlipidemia | 2 | 0 | 0% |
| Total | 37 | 11 | 30% |
| DNA | | | |
| Liver DNA | | | |
| ps C | 14 | 2 | 14.3% |
| Healthy | 4 | 0 | 0% |
| PBC | 9 | 0 | 0% |
| Sarcoid | 1 | 0 | 0% |
| Total | 28 | 2 | 7.1% |
| Colon DNA | | | |
| UC | 25 | 0 | 0% |
| Crohns' | 14 | 0 | 0% |
| Healthy | 8 | 0 | 0% |
| Total | 47 | 0 | 0% |
| Serum DNA | | | |
| HBV | 5 | 0 | 0% |
| CA98C PBMC | 20 | 0 | 0% |
| CA98D serum | 40 | 0 | 0% |
| Total | 65 | 0 | 0% |

6.2. PSC Pol Sequence from Exogenous Retrovirus

The PCR studies of the serum and liver indicated that the PSC pol sequence was probably derived from an exogenous retrovirus, as the sequence was only detected in genomic DNA of 2 PSC patients. Nevertheless, the sequence was found in the majority of the serum and hepatic cDNA samples from PSC patients and thus appears to be associated with PSC. The sequence was also observed in the liver and serum of patients with autoimmune hepatitis. The diagnosis of autoimmune hepatitis is based on the detection of specific autoantibodies inpatients with hepatitis, in the absence of known viral hepatitis, biliary disease, metabolic liver disease, alcoholic liver disease and drug induced liver disease. These diagnostic criteria are essentially based on negative findings and the question has been raised that this idiopathic disorder is heterogeneous in nature and may represent several different diseases. In fact, it has been suggested that some subgroups of autoimmune hepatitis occur as a sequelae to infection with known or unidentified hepatitis viruses.

6. Identification of a Similar Sequence in AIH Bile

These results raised the possibility that a proportion of patients with autoimmune hepatitis may have infection with the PSC-related agent. As autoimmune hepatitis can be part of the spectrum of liver diseases associated with inflammatory bowel disease, it appeared intuitive that this is the subgroup of patients that may harbor the PSC related virus within the liver. In order to directly address this hypothesis, bile was collected from a patient with autoimmune hepatitis and ulcerative colitis. The bile was processed as described in protocols 1–4: viral preparation, RNA extraction, cDNA synthesis, and PCR amplification using the modified degenerate PCR primers to isolate any packaged retroviral genomic sequences in the bile. All autoimmune hepatitis clones isolated and sequenced (table 6) had 95%–98% homology to the previously detected PSC pol sequences (table 3).

7. Construction of PSC Hepatic cDNA Library

For two PSC patients, the PCR products of hepatic cDNA using the PSC pol primers revealed identifiable bands on the ethidium bromide stained agarose gel. A cDNA library was constructed using mRNA extracted- from both these PSC livers by Stratagene. The mass excised plasmids from the PSC library was screened by Gibco BRL using Genetrapper™ methodology and oligonucleotide primers complementary to the novel PSC clone. This library is screened for viral clones that are expected to have additional novel sequences.

TABLE 6

Novel clones identified in autoimmune hepatitis bile.

NB6-e27.3r
TTGGAAGGTGTTGC-CANAGGGATGAAGTTTCCAATCGAATTCACCTATG

GTTATATTCATTTATTCGACTCCTTTCTCTTTATTCCTCACCATTAATTT

TCTTGCCCAAGTACATGGATG

NB6-e27.4r
AGG-ATAAAGTTTCCAATCGAATTCACCTATGGTTATATTCATTTATTCG

ACTCCTTTCTCTTTATTCCTCACCATTAATTTTCTTGCCCAAGTACATGG

AT

NB6-e27.5r
CTTTGGAAGGTGTTGCCCCAAGG-ATAAAGTTTCCAATC-AATGCACCTA

TGGTTATATTCATTTATTCGACTCCTTTCTCTTTATTCCTCACCATTAAT

TTTCTTGCCCAAGTACATGGAT

NB6-e27.15r
TTTGGAAGGTGTTGCNNNAGGGAATAAAGTTTCCAATCGAATTCACCTAT

GGTTATATTCATTTATTCGACTCCTTTCTCTTTATTCCTCACCATTAATT

TTCTTGCCCAAGTACATGGA

Equivalents

It will be appreciated that the methods and compositions of the present invention are capable of being incorporated in the form of a variety of embodiments, only a few of which have been illustrated and described above. While specific examples have been provided, the above description is illustrative and not restrictive. The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within the scope of the invention.

All publications and patent documents cited in this application are incorporated by reference in their entirety for all purposes to the same extent as if each individual publication or patent document were so individually denoted.

What is claim is:

1. A method for identifying an individual having a disorder comprising a step of detecting a presence or absence of a Primary Sclerosing Cholangitis, hereinafter, PSC, associated retroviral nucleic acid molecule, wherein said nucleic acid molecule comprises SEQ ID NOs: 1, 2, 3,4, 5, 6, 7, or the compliment thereof, wherein the presence of the retroviral nucleic acid molecule indicates that the individual has a disorder selected from the group consisting of PSC, Autoimmune Hepatitis, hereinafter AIH, Crohn's disease, and ulcerative colitis.

2. A composition comprising an isolated Primary Sclerosing Cholangitis, PSC, associated retrovirus encoded by a genome comprising a nucleotide sequence comprising SEQ. ID. NOs. 1, 2, 3,4, 5, 6, 7, or the compliment thereof.

3. A method for identifying an individual infected with the Primary Sclerosing Cholangitis, hereafter PSC, associated retrovirus comprising detection of a PSC associate retroviral nucleic acid molecule wherein said nucleic acid molecule comprises SEQ. ID. NOs. 1, 2, 3, 4, 5, 6, 7, or the compliment thereof, wherein the presence of the nucleic acid molecule indicates that the individual is infected with the PSC associated retrovirus.

4. A method for identifying an in vitro sample infected with the Primary Sclerosing Cholangitis, hereafter PSC, associated retrovirus comprising the step of detecting the presence or absence of the PSC associated Retroviral nucleic acid molecule wherein said nucleic acid molecule comprises SEQ. ID. NOs. 1, 2, 3, 4, 5, 6, 7, or the compliment thereof, wherein the presence of the nucleic acid molecule indicates that the sample is infected with the PSC associated retrovirus.

* * * * *